US006905454B2

(12) United States Patent
Gutierrez

(10) Patent No.: US 6,905,454 B2
(45) Date of Patent: Jun. 14, 2005

(54) HANDHELD AND HAND-POWERED CENTRIFUGE DEVICE

(75) Inventor: Anthony G. Gutierrez, Stewartstown, PA (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 10/608,003

(22) Filed: Jun. 30, 2003

(65) Prior Publication Data

US 2004/0063561 A1 Apr. 1, 2004

Related U.S. Application Data

(60) Provisional application No. 60/391,945, filed on Jun. 28, 2002.

(51) Int. Cl.[7] .............................. B04B 5/02; B04B 9/00
(52) U.S. Cl. .......................................... 494/16; 494/84
(58) Field of Search .............................. 494/16, 31, 33, 494/43, 84, 85

(56) References Cited

U.S. PATENT DOCUMENTS

| 780,315 A | 1/1905 | Wetherill |
|---|---|---|
| 3,233,825 A | 2/1966 | Lomb |
| 3,268,160 A | 8/1966 | Talley |
| 4,738,655 A | 4/1988 | Brimhall et al. |

*Primary Examiner*—Charles E. Cooley
(74) *Attorney, Agent, or Firm*—Elizabeth Arwine

(57) ABSTRACT

This invention relates to a handheld, hand-powered centrifuge device. The device preferably includes a centrifuge body and a sample-holding member connected to a tether. The device centrifuges the sample by a user physically spinning the member preferably in a vertical arc. The device preferably includes a pull handle which allows a user to shorten the length of the tether to reduce the circumference of the arc, thereby increasing the speed of rotation and centrifugal force on the sample. The device also preferable includes a brake to prevent the member from contacting the handheld centrifuge body. The centrifuge body may have a storage cavity for storing the pull handle when not in use, wherein the member serves to seal the storage cavity when not in use.

14 Claims, 6 Drawing Sheets

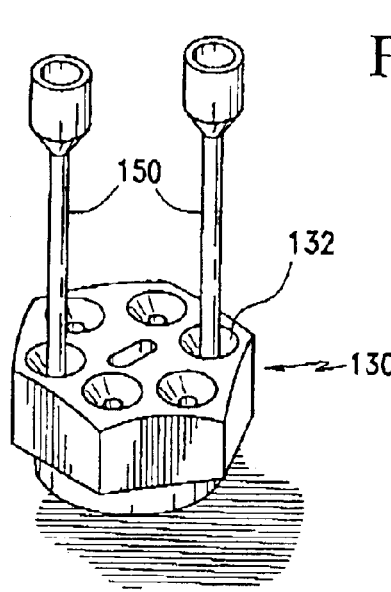
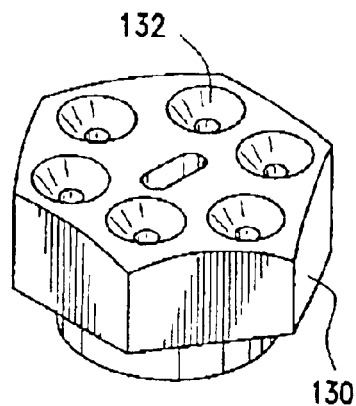
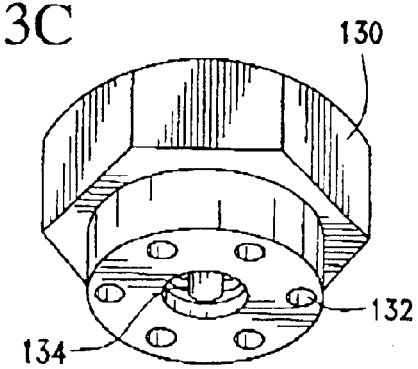
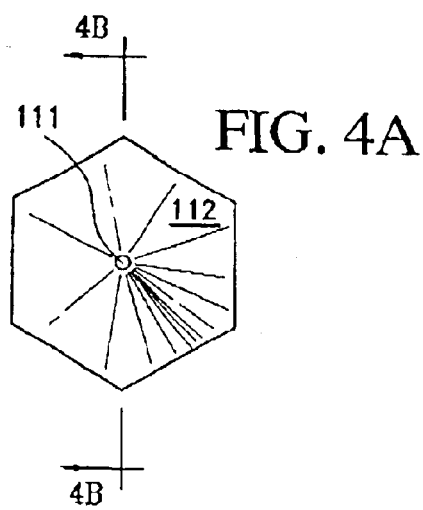
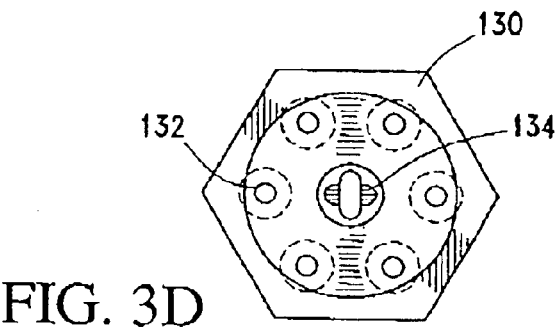
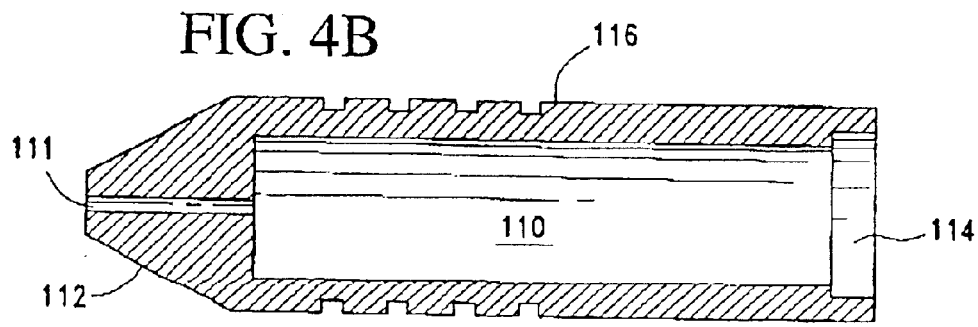

HANDHELD AND HAND-POWERED CENTRIFUGE DEVICE

This application claims the benefit of U.S. provisional Application Ser. No. 60/391,945, filed Jun. 28, 2002, which is hereby incorporated by reference.

I. FIELD OF THE INVENTION

This invention relates to centrifuge devices. More particularly, this invention relates to portable, handheld and hand-powered centrifuge devices, and methods of using the same.

II. BACKGROUND OF THE INVENTION

Centrifuge devices are known in the art. In particular, centrifugation as a means of accelerating sedimentation of precipitates and particulates has long been an integral part of biochemical protocols. A typical centrifuge consists of a rotor encased in a housing. The rotor is powered by a drive motor or some other electrical or battery powered force that allows it to rotate.

Separation of the samples occurs because each component has a different density and thus a different sedimentation velocity. Sedimentation velocity is a measure of how fast a component will migrate through other more buoyant sample components as a result of the centrifugal field generated by the spinning centrifuge.

With polymerase chain reaction (PCR) devices, for example, it will be appreciated that thermocyclers are currently shipped with a benchtop nanocentrifuge. The nanocentrifuge is needed to force the liquid reaction mix to the bottom of a capillary tube before any analysis can be performed. As will be appreciated, these devices suffer from many drawbacks. For example, benchtop nanocentrifuges are delicate, expensive, and ill-suited for field use. In particular, these devices have many small parts and are not rugged or durable. Furthermore, in addition to the delicacy of its components, these devices also require 110 V outlets to power the rotor. Even if a remote power source is used, such as batteries, the device assumes an impractical weight for portable and reliable field use.

The foregoing underscores some of the problems associated with conventional centrifuge devices. Furthermore, the foregoing highlights the need in the art for a portable, durable centrifuge device and the need in the art for a centrifuge device not requiring an electrical or battery power source.

III. SUMMARY OF THE INVENTION

The present invention overcomes the aforementioned drawbacks in the art and offers new advantages as well. Accordingly, it is an object of the invention to provide a portable and durable centrifuge device capable of reliable field use. It is also an object of the invention to provide a portable, durable centrifuge device not requiring an electrical power source. In accordance with these objects of the invention, there is provided a handheld, hand-powered centrifuge device.

According to one aspect of the invention, the centrifuge device is adapted for PCR methods.

According to one aspect of the invention, the device is configured for centrifuging glass capillary tubes used by hot air mediated PCR thermocyclers such as the Lightcycler by Roche or the R.A.P.I.D. by Idaho Technologies.

According to one aspect of the invention, the device is configured for performing hematocrit type blood separations for field diagnostics.

At least one embodiment of the invention includes a handheld centrifuge device including a centrifuge body adapted for handling by a user, a holder adapted for holding at least one sample to be centrifuged, and a tether having a first end associated with said centrifuge body and a second end associated with said holder.

At least one embodiment of the invention includes a centrifuge device including a centrifuge body having an open back end, a conical front end, a hand portion, and defining a passageway therethrough; a tether extending through said passageway and having a first end extending away from said conical front end and a second end extending into said open back end; a pull handle sized to fit in said open back end, said pull handle being attached to said second end of said tether; and a holder having at least two apertures for receiving sample tubes to be centrifuged, said holder being connectable to said first end of said tether.

At least one embodiment of the invention includes a handheld centrifuge device including a centrifuge body adapted for handling by a user; a sling adapted for holding a sample to be centrifuged; and a tether attached to said sling and in communication with said centrifuge body.

At least one embodiment of the invention includes a centrifuge device including means for holding at least one specimen, means for increasing centrifugal force on the at least one specimen, and means for providing a rotation axis.

An exemplary embodiment of the invention includes a device having a sample holder (or member), a centrifuge body and a tether. The exemplary embodiment includes a sample holder adapted to receive a sample, or samples, wherein the sample holder is connected to a tether in communication with a handheld centrifuge body. In this exemplary embodiment, the handheld centrifuge body may be manipulated by a user to exert a centrifugal force on the sample. Preferably, the force is created by a user manipulating the centrifuge body to spin the sample holder in a circle via the tether. The exemplary embodiment also includes a pull handle, which allows a user to manipulate the length of the tether extending from the centrifuge body, and thus the speed of the centrifugal rotation. A modification of the exemplary embodiment adds a brake to the device. Preferably, the brake is configured to prevent the sample holder and/or samples from hitting the centrifuge body. In the modified exemplary embodiment, the brake includes flexible tubing.

An exemplary embodiment of the invention includes a handheld device having a sample holder, a centrifuge body, a pull handle, and a tether. In this exemplary embodiment, the sample holder and pull handle are preferably attached by the tether, which has a predetermined length. Preferably, the tether is configured to have a small diameter, e.g., wire, string, etc. In the exemplary embodiment, the tether includes a two-foot coated length of string, such as waxed nylon string, which is preferably threaded through the centrifuge body to join the pull handle and the sample holder. In the exemplary embodiment, the tether includes a T-bar on one end dedicated to engaging the sample holder.

At least one of the exemplary embodiments includes a centrifuge body preferably configured to fit in the hand of a user, and preferably has a passageway extending through its body to allow passage of the tether. The centrifuge body in this exemplary embodiment is conical on its end proximal to the sample holder. In this exemplary embodiment, the centrifuge body is provided with a storage compartment configured for engaging and storing the sample holder when not in use.

In at least one exemplary embodiment, the sample holder is configured to accept a capillary tube or tubes in a passageway or passageways in its body. The sample holder preferably includes a cylinder with six evenly spaced openings disposed around its circumference and sized to accept capillary tubes.

In at least one exemplary embodiment, a pull handle is provided to allow a user to pull the tether through the centrifuge body to manipulate the length of tether, and thus the speed of the rotation of the sample holder. In at least one exemplary embodiment, at least a portion of the pull handle fits into an open cavity provided in the centrifuge body, and preferably all of the pull handle may be stored in the centrifuge body when not in use.

In at least one exemplary embodiment, a brake mechanism is provided, which preferably serves to keep the sample holder and samples from contacting the centrifuge body. The brake preferably includes flexible tubing disposed around a portion of tether. In at least one exemplary embodiment, the brake serves to engage the T-bar of the tether with the sample holder by holding the T-bar firmly against the blind end of a 90-degree intersecting oval drilled from the bottom of the rotor.

Given the following enabling description of the drawings, the apparatus should become evident to a person of ordinary skill in the art.

IV. BRIEF DESCRIPTION OF THE DRAWINGS

The present invention is described with reference to the accompanying drawings. In the drawings, like reference numbers indicate identical or functionally similar elements.

Figure 1:
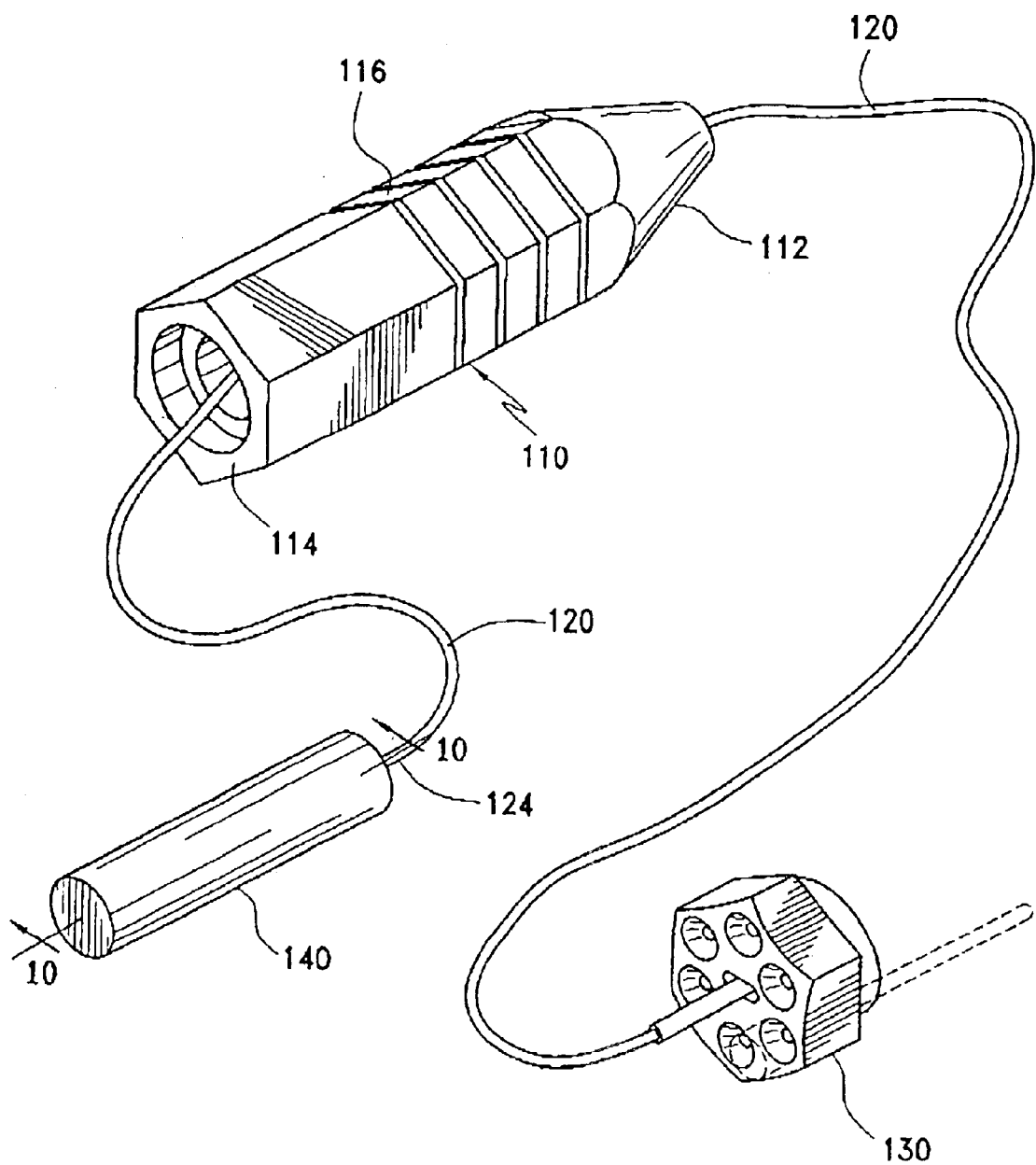
FIG. 1 illustrates an exemplary embodiment according to the invention.
Figure 2:
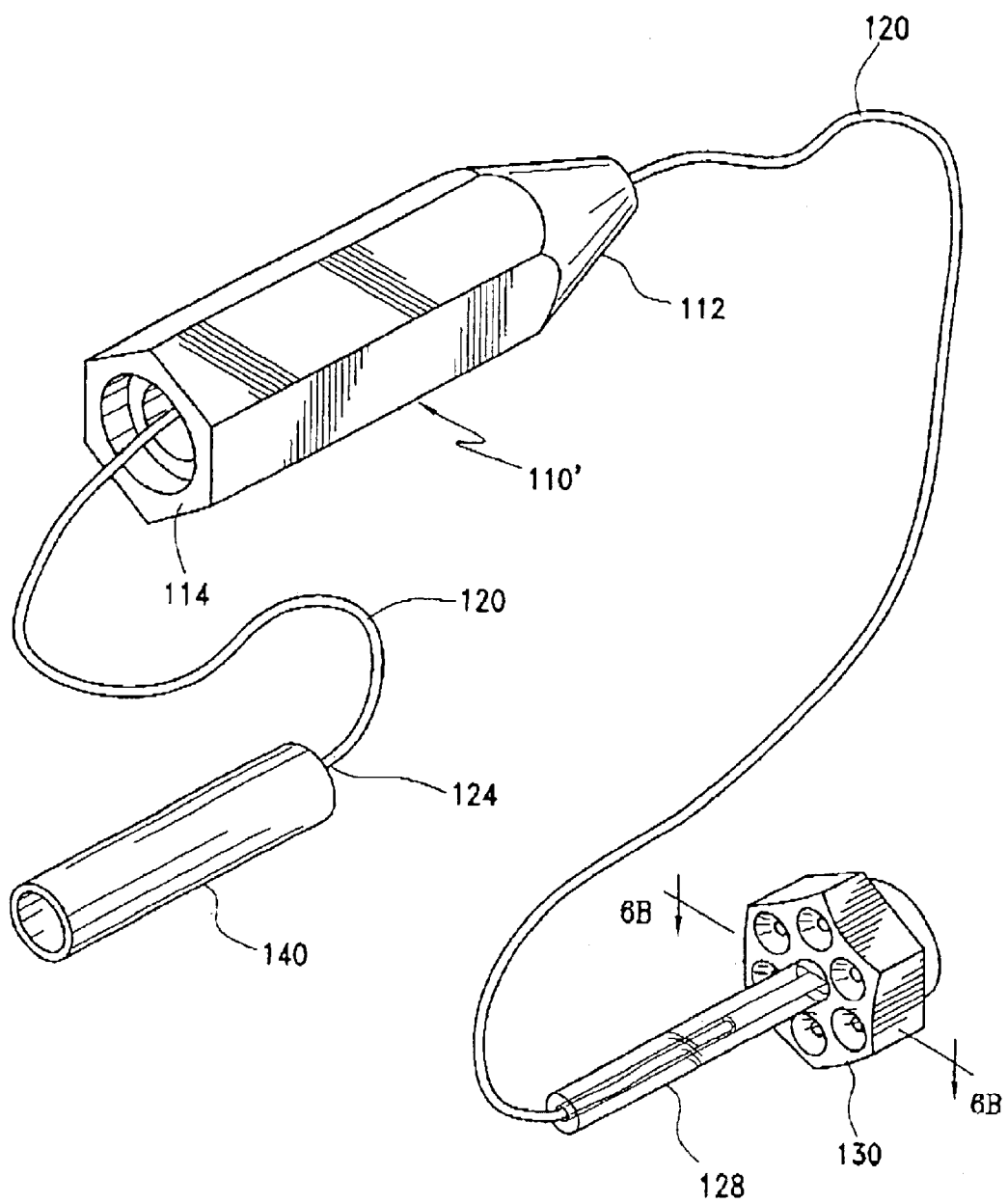
FIG. 2 depicts an alternative configuration for the exemplary embodiment illustrated in FIG. 1.

FIGS. 3A-D illustrate different views of the specimen holder from the exemplary embodiments shown in FIGS. 1 and 2.

FIGS. 4A and B depict the centrifuge handle from the exemplary embodiment shown in FIG. 1.

Figure 5:
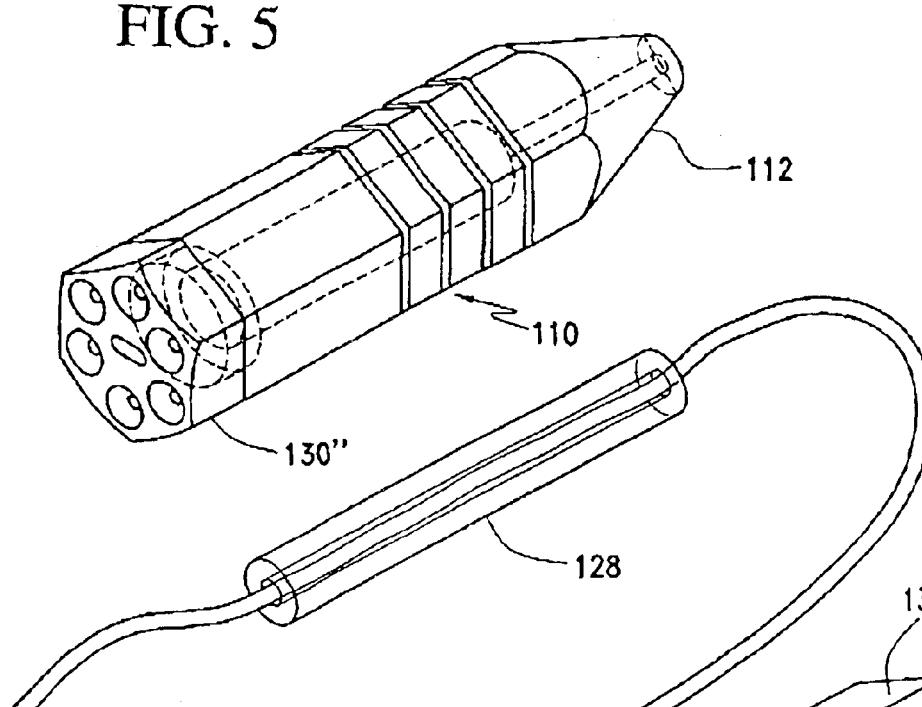

FIG. 5 illustrates the exemplary embodiment of FIG. 1 in a storage state.

Figure 6A:
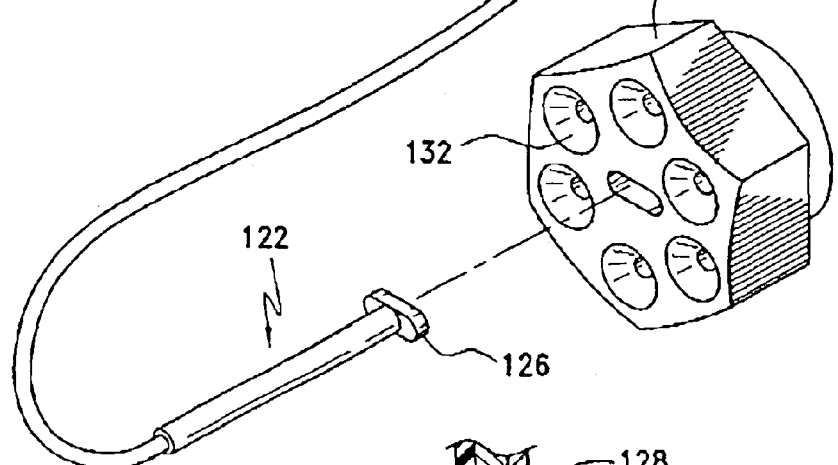

FIG. 6A depicts the T-bar, brake, and a portion of the tether of the exemplary embodiment shown in FIG. 2.

Figure 6B:
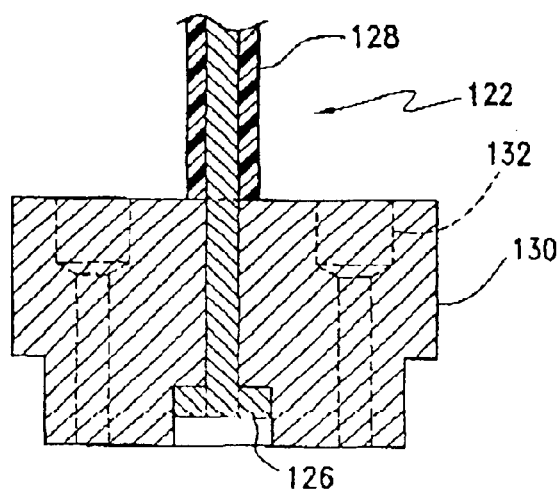

FIG. 6B depicts a cross-section of the assembled pieces from FIG. 6A.

Figure 7:
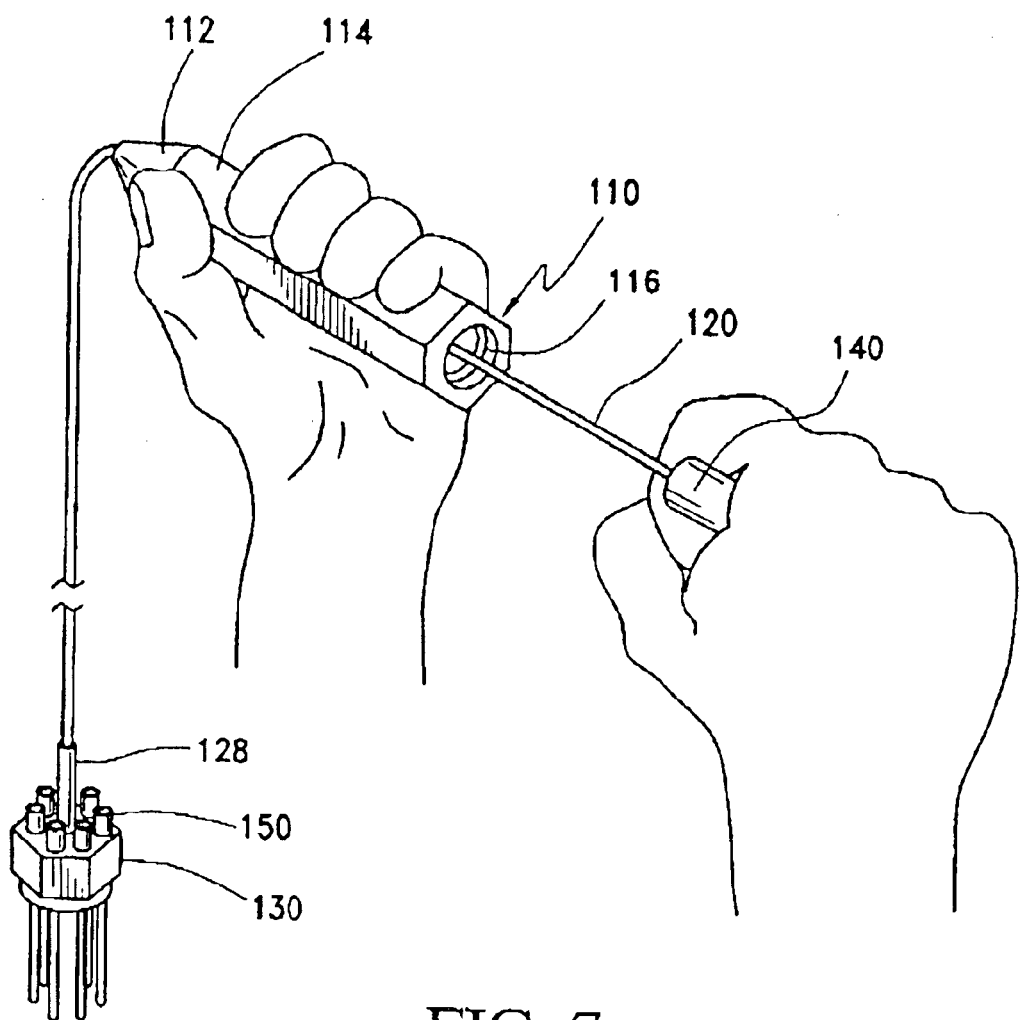

FIG. 7 illustrates how the exemplary embodiment might be used as a centrifuge.

Figure 8A:
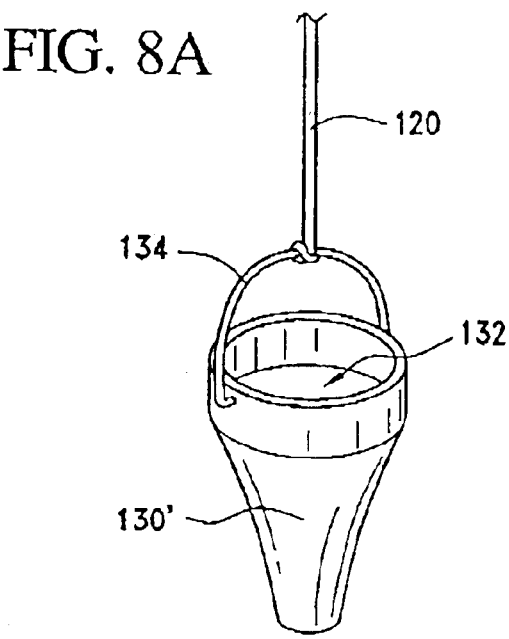

FIGS. 8A and B depict another set of exemplary embodiments according to the invention.

Figure 9A:
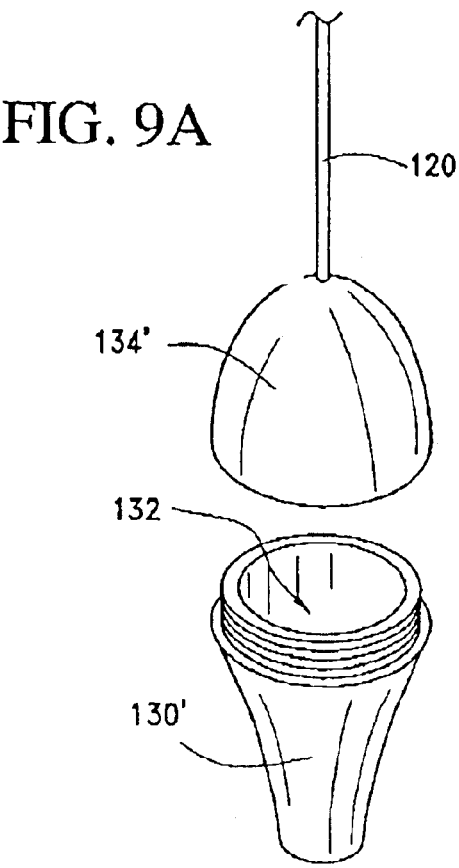

FIGS. 9A and B illustrate another set of exemplary embodiments according to the invention.

Figure 10:
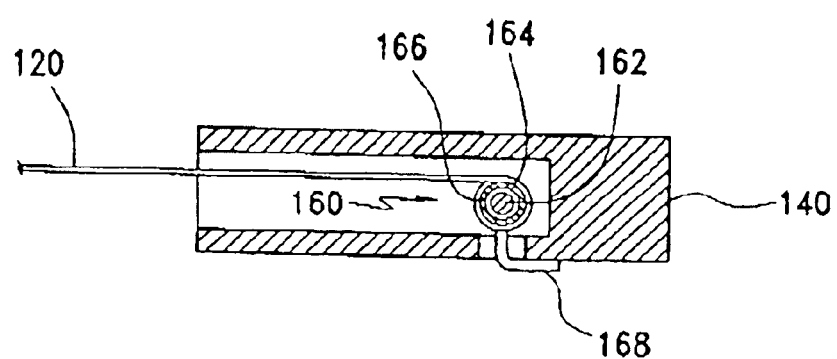

FIG. 10 depicts an alternative embodiment for the handle according to the invention.

IV. DETAILED DESCRIPTION OF THE EXEMPLARY EMBODIMENTS

The present invention is based, in part, on the concept that a human user can generate a centrifugal force on a specimen (or sample) holder (or member) if provided with a tether. While the present invention will be described in connection with a PCR centrifuge device, it will be readily apparent to one of ordinary skill in the art that the present invention can be applied to a multiplicity of fields and uses. In general, the present invention may be used in any field for any task requiring a centrifugal force be applied to a specimen, which is held in a specimen holder. Exemplary types of specimen holders (or means for holding at least one sample) include a multispecimen holder and a sling as described below and illustrated in the figures. The specimen holder preferably is lightweight and balanced to increase the rate at which the specimen holder may be spun about a handle as illustrated by one exemplary embodiment in FIG. 7. The present invention is particularly adapted for field uses, or other applications wherein an electrical power source is unavailable or impractical.

The invention at its basic level preferably includes a hollow handheld tube (or conduit) 110 with a small hole 111 at one end through which a spinning tether 120 can be hand drawn through to magnify the centrifugal force on a sample (or specimen) holder 130 at the end of the tether 120. The tether 120 preferably is attached to a handle 140 at the end opposite the sample holder 130 to allow the user to have more control over the pulling of the tether 120 through the tube 110.

An exemplary embodiment of the invention is depicted in FIGS. 1–2. As depicted, centrifuge device includes centrifuge body (or centrifuge handle) 110, which has conical front end 112, open back end 114 and palm part 116. Palm part 116 is preferably configured to fit in the hand of a user, who manipulates the body 110 to generate a centrifugal force as described herein and illustrated in FIG. 7. FIG. 2 illustrates an exemplary embodiment for centrifuge body 110' has a smooth and simpler surface than the grooved configuration of centrifuge body 110 in FIG. 1. The illustrated grooves improve the grip of the user over what is possible with the polygonal cross-section.

Extending through centrifuge body 110 is preferably tether 120. Tether 120 preferably includes wire, string, or like material, which has a small diameter and is capable of being spun to generate a centrifugal force on a body. Tether 120 more preferably is a two-foot coated length of string, such as waxed nylon string.

Tether 120 is preferably threaded through centrifuge body 100 and has a front end 122 attachable to multispecimen holder 130 and a back end 124 either held by centrifuge body 110 (not shown), or preferably, attached to pull handle 140. Alternatively, back end 124 may be a free end. To aid the attachment to multispecimen holder 130, tether 120 may be provided with T-bar 126 (best shown on FIG. 6A).

Multispecimen holder 130 is provided with passageways or recesses 132 for accepting capillary tubes 150 to be centrifuged. Multispecimen holder 130 as illustrated in the exemplary embodiments shown in FIGS. 1–3D, 6A, and 7 includes six passageways 132. Multispecimen holder 130 may alternatively be a plate with holes passing through it omitting the illustrated cylindrical portion.

An alternative embodiment for these exemplary embodiments is that multispecimen holder 130 may be used as a sample rack as depicted in FIG. 3A.

Pull handle 140 serves to allow a user to shorten the length of tether 120 extending from conical front end 112 of centrifuge body 110, thereby increasing the rate of speed at which multispecimen holder 130 is spun. As will be appreciated, the final rotations of the multispecimen holder 130 should be at an extremely high speed to ensure the sample is driven to the bottom of the tubes 150. Accordingly, a swift pull of the pull handle 140 away from centrifuge body 110 is particularly advantageous.

Preferably, brake 128 as illustrated in the exemplary embodiment of FIG. 2 is provided to prevent multispecimen holder 130 or tubes 150 from contacting centrifuge body 110, particularly when pull handle 140 is swiftly pulled away from centrifuge body 110. In this exemplary embodiment, brake 128 includes a piece of flexible tubing disposed around tether 120 and adjacent or connected to multispecimen holder 130. As will be appreciated, brake 128 is sized such that it cannot pass through the opening in conical front end 112 of centrifuge body 110, thereby ensuring a safe distance separates multispecimen holder 130 from body 110 to prevent contact, i.e., a collision between the two pieces.

Although not depicted, a flexible tubing brake may also serve as a grip or locking piece for engaging T-bar 126 of tether 120 with multispecimen holder 130 by holding it firm against a blind end of a 90-degree intersecting oval 134 (shown in FIGS. 3C and 3D) drilled from the bottom of multispecimen holder 130.

In another exemplary embodiment illustrated in FIG. 5, the pieces are preferably sized such that the tether 120 and pull handle 140 can fit inside the centrifuge body 110 and be held in place by screwing multispecimen holder 130" into threads disposed in open back end 114 of body 110 to seal the storage compartment. As will be appreciated, this helps make the device extremely portable. If desired, the device could be housed in a pocket, belt sheath, or the like. Furthermore, the threading of the pieces via the tether 120 makes it virtually impossible to lose any of the associated pieces. Multispecimen holder 130" is preferably still removable from tether 120 so that it can be used as a stable sample rack (as shown in FIG. 3A) and/or closure for open back end 114 of body 110 (as shown in FIG. 5). Also preferably storable in centrifuge body 110 is pull handle 140 in this exemplary embodiment.

An advantageous feature of the invention is that the device requires no electrical or battery power source. The unit is operated by a user who spins and pulls the device to generate the centrifugal force. In operation the device works as follows. Capillary tubes 150 are filled with a sample and placed in the dedicated tube passageways 132 in multispecimen holder 130. Multispecimen holder 130 is connected to front end 122 of tether 120 via T-bar 126.

The user grips hand portion 116 of body 110 and suspends the multispecimen holder 130 from the body 110 via tether 120 as illustrated in FIG. 7. The user manipulates centrifuge body 110 to cause tether 120 to rotate multispecimen holder 130 preferably in a vertical arc, thereby exerting a centrifugal force on samples in tubes 150. The user engages pull handle 140 and rapidly pulls it away from body 110, thereby shortening tether 120 extending from conical front end 112 of body 110 to ensure the final rotations of the multispecimen holder 130 are at an extremely high speed to finish driving the samples to the bottom of the tubes 150. Brake 128 (in the exemplary embodiments with it) serves to prevent multispecimen holder 130 from contacting front end 112.

Another set of exemplary embodiments according to the invention is for performing hematocrit blood separation and is capable of higher centrifugal forces being applied to the specimen. FIGS. 8A–9B illustrate different versions of these exemplary embodiments, which includes a sling 130' for holding the specimen vial 150 in place of multispecimen holder 130 in the prior exemplary embodiments. Sling 130' in the exemplary embodiments shown in FIGS. 8A–9B includes a conical shaped member (or vessel) that includes an inner cavity (or passageway) 132' sized to hold capillary tube 150 and is similar to passageways 132 passing through multispecimen holder 130 for holding the specimen vials 150. The illustrated slings 130' preferably are each lightweight and streamlined to fit around the specimen vial 150, and as such can take a variety of shapes to facilitate holding a specimen vial 150.

Figure 8B:
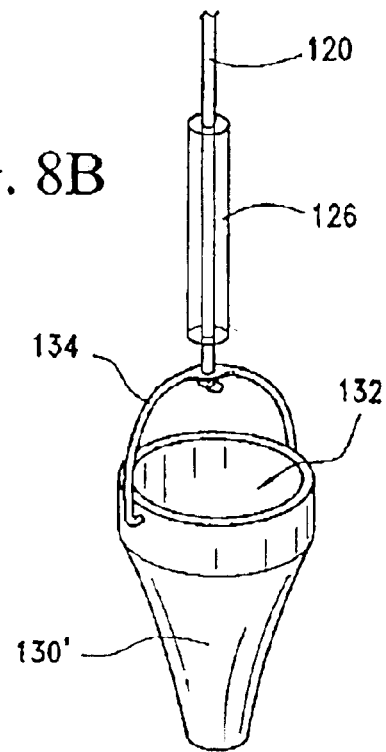

FIGS. 8A and 8B illustrate sling 130' attached to a handle 134 that preferably is pivotally connected to the sling 130' such that the handle may be pivoted away from the top of the passageway 132 to allow insertion of capillary tube 150. FIG. 8A illustrates the tether 120 being attached to the handle with a knot although one of ordinary skill in the art will realize that a variety of ways exist to attach the handle 134 to the tether 120. Another example of a connection between handle 134' and tether 120 is shown in FIG. 8B where the tether 120 passes through the handle 134. FIG. 8B also illustrates the presence of a brake 128.

Figure 9B:
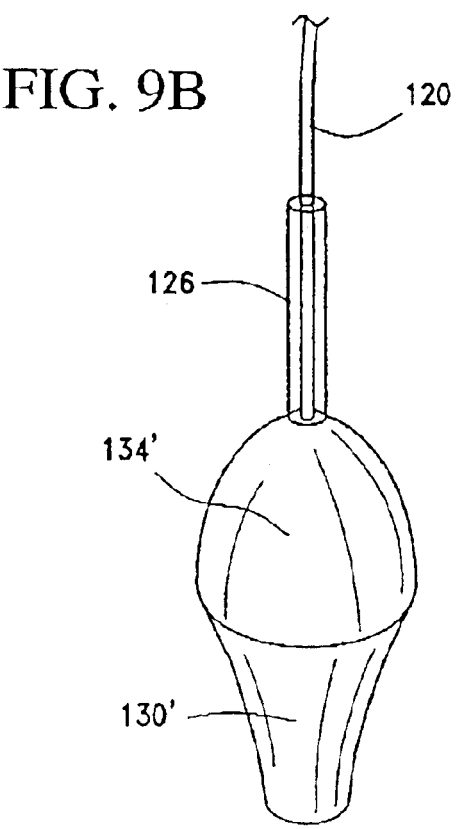

FIGS. 9A and 9B illustrate a different way to attach the sling 130 ' to the tether 120. The handle 134' in these exemplary embodiments is a cover that is threaded to be able to screw onto the sling 130'. The handle (or cover) 134' then attaches to the tether 120. FIG. 9B illustrates an exemplary embodiment that includes brake 128. The sling 130' and handle 134' in the exemplary embodiment illustrated in FIG. 9A and 9B preferably is made with a polypropylene material or other similar lightweight and sturdy material.

Another exemplary embodiment adds a spring mechanism 160 in the handle 140 (as illustrated in FIG. 10), although an alternative embodiment places the spring mechanism 160 in the centrifuge body 110 and eliminates the handle since the tether 120 would terminate inside of the centrifuge body 110 (not shown although it would have a similar arrangement as illustrated in FIG. 10). The spring mechanism 160 allows for a consistent level of centrifugal force to be applied to the specimen(s) being spun so that from one use to another there is a consistent pull of the tether 120, which is critical for performing hematocrit blood separation. The spring mechanism 160 preferably is perpendicular to the tether 120. An exemplary version of the spring mechanism 160 includes an axel 162 connected to a spring 164 which wraps around the axel 162. The spring 164 in turn is connected to a spindle (or reel) 166. The spindle 166 acts as the reel and storage point for the tether 120. The spring mechanism 160 preferably also includes a ratchet mechanism 168 that is set by the user and allows for the tether 120 to be pulled out and secured in that pulled out state, and when the user wishes to retract the tether 120 as part of the centrifuge process, the user begins the spin of the specimen holder 130 (for at least one revolution) before releasing the spindle 166 to retract the tether 120 by disengaging the ratchet mechanism 168 from the spindle 166.

The exemplary devices may be comprised of any suitable material of construction. It is preferred that the device is constructed of materials, which ensure the durability and portability of the device. The exemplary embodiments show centrifuge body 110 and multispecimen holder 130 that are machined from a solid hexagonal (or other polygonal shape) rod preferably made of aluminum (or like material). This configuration and material help ensure that the pieces will not role off uneven surfaces common in the field, and also ensure the virtual indestructibility of the pieces even under the most extreme field conditions. Pull handle 140 is preferably made from a solid cylindrical aluminum rod. Sling 130' preferably is made from a light material such as aluminum or ploypropylene.

An alternative way to view the invention includes a means for holding at least one specimen (holding means), a means for increasing centrifugal force on the at least one specimen (force means), and a means for providing a rotation axis (rotation axis means). The holding means includes any of the above-described specimen holders including the multispecimen holder 130 and sling 130'. The force means includes the pull handle 140 used to shorten the length of tether 120 and thus the radius of rotation for the specimen and/or spring mechanism 160 in conjunction with either the pull handle 140 or the centrifuge handle 110. The force means also includes the tether 120 which provides the radial distance of the rotation for the specimen. The rotation axis means includes the centrifuge handle 110 or any other member capable of allowing the user to control the center of rotation of the specimen.

Although the present invention has been described in terms of particular exemplary embodiments, it is not limited to those embodiments. Alternative embodiments, examples, and modifications which would still be encompassed by the invention may be made by those skilled in the art, particularly in light of the foregoing teachings. The exemplary and alternative embodiments described above may be combined in a variety of ways with each other. Furthermore, the dimensions, shapes, sizes, and number of the various pieces illustrated in the Figures may be adjusted from that shown.

Furthermore, those skilled in the art will appreciate that various adaptations and modifications of the above-described exemplary embodiments can be configured without departing from the scope and spirit of the invention. Therefore, it is to be understood that, within the scope of the appended claims, the invention may be practiced other than as specifically described herein.

What is claimed is:

1. A handheld centrifuge device comprising:
   a centrifuge body adapted for handling by a user;
   a holder adapted for holding at least one sample to be centrifuged; and
   a tether having a first end associated with said centrifuge body and a second end associated with said holder,
   a pull handle connected to said first end of said tether; and
   wherein said tether said is connected to said holder by a T-bar.

2. A handheld centrifuge device comprising:
   a centrifuge body adanted for handling by a user;
   a holder adapted for holding at least one sample to be centrifuged; and
   a tether having a first end associated with said centrifuge body and a second end associated with said holder,
   a pull handle connected to said first end of said tether; and
   wherein said centrifuge body defines a cavity on an open back end, and wherein said pull handle is configured to be disposable in said cavity.

3. The centrifuge device of claim 2, wherein said holder is configured to seal said open back end of said centrifuge body.

4. The centrifuge device of claim 2, wherein said open back end is threaded for receiving threads disposed on said holder.

5. A handheld centrifuge device comprising:
   a centrifuge body adapted for handling by a user;
   a holder adapted for holding at least one sample to be centrifuged; and
   a tether having a first end associated with said centrifuge body and a second end associated with said holder,
   a pull handle connected to said first end of said tether; and
   a brake disposed around an area of said second end of said tether.

6. The centrifuge device of claim 5, wherein said brake includes flexible plastic tubing.

7. The centrifuge device of claim 6, wherein said tether includes a two-foot length of waxed nylon string.

8. A handheld centrifuge device comprising:
   a centrifuge body adapted for handling by a user;
   a holder adapted for holding at least one sample to be centrifuged; and
   a tether having a first end associated with said centrifuge body and a second end associated with said holder,
   wherein said handle includes a spring mechanism attached to said tether.

9. A handheld centrifuge device comprising:
   a centrifuge body adapted for handling by a user;
   a holder adapted for holding at least one sample to be centrifuged; and
   a tether having a first end associated with said centrifuge body and a second end associated with said holder;
   wherein said centrifuge body and said holder are machined from solid hexagonal aluminum rod, and
   wherein said holder defines six evenly spaced apertures for receiving sample tubes disposed around its circumference.

10. A centrifuge device comprising:
    a centrifuge body having an open back end, a conical front end, a hand portion, and defining a passageway therethrough;
    a tether extending through said passageway and having a first end extending away from said conical front end and a second end extending into said open back end;
    a pull handle sized to fit in said open back end, said pull handle being attached to said second end of said tether; and
    a holder having at least two apertures for receiving sample tubes to be centrifuged, said holder being connectable to said first end of said tether.

11. The centrifuge device according to claim 10, wherein said holder is connectable to said open back end of said centrifuge body.

12. The centrifuge device according to claim 10, wherein said pull handle includes a spring mechanism.

13. A handheld centrifuge device comprising:
    a centrifuge body adapted for handling by a user;
    a sling adapted for holding a sample to be centrifuged; and
    a tether attached to said sling and in communication with said centrifuge body,
    wherein said sling includes
    a handle attached to said tether, and
    a conduit connected to said handle, said conduit having a passageway passing therethrough, the passageway shaped to nest a specimen container.

14. A handheld centrifuge device comprising:
    a centrifuge body adapted for handling by a user;
    a sling adapted for holding a sample to be centrifuged; and
    a tether attached to said sling and in communication with said centrifuge body, and
    a spring mechanism attached to said tether.

* * * * *

UNITED STATES PATENT AND TRADEMARK OFFICE
CERTIFICATE OF CORRECTION

PATENT NO. : 6,905,454 B2
DATED : June 14, 2005
INVENTOR(S) : Anthony G. Gutierrez It is certified that error appears in the above-identified patent and that said Letters Patent is hereby corrected as shown below:

Column 7,
Line 41, after "tether" delete "said";
Line 44, change "adanted" to -- adapted --.

Signed and Sealed this

Sixth Day of September, 2005

JON W. DUDAS
*Director of the United States Patent and Trademark Office*